United States Patent [19]

Tullis et al.

[11] Patent Number: 5,004,340
[45] Date of Patent: Apr. 2, 1991

[54] CALIBRATION TARGET FOR SURFACE ANALYSIS SCANNER SYSTEMS

[75] Inventors: Barclay J. Tullis, Palo Alto; James B. Kruger, Half Moon Bay, both of Calif.

[73] Assignee: Hewlett-Packard Company, Palo Alto, Calif.

[21] Appl. No.: 186,879

[22] Filed: Apr. 27, 1988

[51] Int. Cl.⁵ .............................. G01N 21/88
[52] U.S. Cl. ...................................... 356/243
[58] Field of Search .................... 356/243, 38

[56] References Cited

U.S. PATENT DOCUMENTS 4,767,660  8/1988  Hosoda et al. ................. 356/243
4,776,693 10/1988  Imamura et al. .............. 356/243

FOREIGN PATENT DOCUMENTS 8500885  3/1985  PCT Int'l Appl. .............. 356/243

*Primary Examiner*—Samuel Turner

[57] ABSTRACT

A surface analysis scanner system includes calibration targets, which include a target substrate and a film covering the surface of the target substrate which is scanned by the surface scanner. The film is antireflective to the particular scanned light. Particles which contaminate the antireflectance film on the substrate do not scatter sufficient light to be detected by the surface analysis scanner detectors and thus do not interfere with the calibration of the scanner. The calibration targets may include reference features which are etched into the substrate surface or deposited on the antireflectance coated substrate surface which scatter light in a manner similar to particles on a surface. The reference features may also be imbedded in a transparent material supported by the antireflectance coated substrate with a second antireflectance film coating the upper surface of the transparent material. A surface analysis scanner system may also include a support structure for supporting an object to be scanned, an aperture structure, and a light trap structure for blocking the scanned light. Each structure includes a substrate having a coating of antireflectance film. A surface analysis scanner system may also include methods, utilizing antireflectance films, for reducing the amount of scanned light scattered by particles on a scanner system surface.

11 Claims, 5 Drawing Sheets

CALIBRATION TARGET FOR SURFACE ANALYSIS SCANNER SYSTEMS

This invention relates to surface analysis scanner systems and more particularly to the use of antireflectance films with such systems to prevent scanning light from being scattered by particles adjacent to a scanned surface.

BACKGROUND OF THE INVENTION

Automated surface analysis systems for detecting surface flaws and particle contamination have many applications, particularly in semiconductor manufacture and research. For example, surface analysis systems can be used to detect surface flaws and contaminating particles on silicon wafers; such flaws and contamination tends to interfere with processing and to reduce the quality of the completed semiconductor device.

Current automated surface analysis systems detect surface defects by light that has been scattered or deflected from an intense illuminating beam directed at the surface being analyzed. The illuminating beam is commonly a focused spot of laser light which is scanned across the surface being inspected. The WIS-600 surface analysis system manufactured by Estak Corporation is one example of current surface analysis systems.

Scanned laser surface analysis systems include a scattered light detector assembly for detecting laser light scattered by specific defects. Scattered-light detectors are particularly useful in detecting surface particles since such particles scatter light. Surface analysis systems may also include an assembly which directly detects reflected laser light for detecting surface defects that cause deviations in surface flatness. The two types of detectors, used together, may detect a broad range of surface defects and contamination.

Referring now to surface particle detection by a surface analysis scanner, light scattered by particles on the scanned surface is collected and converted to electrical signals which are conditioned and then processed by a computer to determine the desired surface information. Threshold signal level and device gain determine the sensitivity of the device to optical signals received by the scattered light detector. The threshold signal level refers to a minimum electrical signal required to produce a response on the system's output device. The lower the threshold setting, the higher the sensitivity of the system to detected light. The gain of the surface analysis device refers to the relationship between the amplitude of the electrical signal generated by the system and the optical signal amplitude received by the detector which converted the optical signal into the electrical signal. The higher the system gain, the greater the signal produced for a given optical signal.

Although the relationship between light scattering amplitude and particle size is not linear or single valued, it is clear that increasing the gain of an instrument changes the size of particle that can be detected by the instrument. Thus, it is critical to meaningful particle counting to hold the system gain constant.

A reference scattering target or calibration target is needed to adjust the instrument gain to a constant level. Such a target must produce reliably repeatable signals and thus must not produce unintentional signals from particle contamination of the target surface.

Once the gain relative to the threshold settings is fixed, what remains is to ensure that all legitimate signals occurring above the desired thresholds, and only those signals, are counted and that some meaningful particle attribute is ascribed to the threshold settings. Again, reference targets having known artifacts or reference features are indispensible in ensuring that only what should be counted is counted. Clearly, contamination of such a reference target by surface particles could disturb the count of reference features.

Several ambiguities hamper the interpretation of light scatter data. The first ambiguity arises from the fact that the relationship between particle size and the amplitude of scattered light is neither linear nor single-valued. Furthermore, there is no existing exact mathematical solution to the problem of relating the portion of incident light scattered by a particle resting on a surface to the particle size or shape. Also it is well documented that the optical properties of a substrate have a significant effect on the optical sizing of a particle. Due to these ambiguities, characterizing parameters are necessary in order meaningfully to compare data from surface analysis instruments.

With regard to scattered light particle detectors, there are seven characterizing parameters of interest. These parameters are sensitivity, counting accuracy, uniformity, dynamic range, spatial resolution, repeatability, and stability. Thus, in addition to fixing system gain relative to the threshold settings, each of the characterization parameters must be determined for a particular instrument in order for its data to be meaningful.

As with gain and threshold setting or calibration, the determination of characterization parameters requires calibration targets having reference features with known light scattering properties. Several types of calibration targets are in current use, including wafers having reference particles dispersed on their surface or a portion thereof, or wafers with point features etched into their surface to simulate effectively a patterned array of particles.

Regardless of the type of calibration target employed, it is crucial that the calibration target itself be free of unintentional particle contamination. If particles other than the reference features exist on the calibration target, light scattered by these unknown particles will be detected along with the light scattered from the known features and will make calibration or parameter determination less precise and less accurate. Thus, a great deal of care must be taken to ensure that current calibration targets are free from contamination which might upset the setting of system gain and thresholds, as well as the determination of the instrument's characterizing parameters.

SUMMARY OF THE INVENTION

Pursuant to the present invention, a reduction is achieved in the amount of light scattered by particles that are contaminating surfaces within an automated surface analysis scanner. The invention encompasses calibration targets which reduce the amount of light scattered by particles contaminating the target surface. Also, a support structure is provided for supporting a surface being analyzed, which prevents scanner light from being scattered by particles contaminating the support surface, and which also prevents reflection of the scanned light from the support surface. The present invention also encompasses aperture and light trap structures, as well as methods, utilizing antireflectance films, for reducing the amount of scanned light scattered by particles on a scanner system surface.

It has been determined that antireflectance films on a substrate surface tend to reduce the amount of light scattered by particles contaminating the film surface. For example, particles in the size range of 0.3 to 5.0 micrometer on an antireflecting silicon nitride film coating a silicon substrate scatter insufficient light from a He—Ne laser beam operating at a wavelength of 0.6328 micrometers to be detected by most of today's surface analysis instruments. Thus, even though these particles may be present on the antireflectance film surface, they are not counted or "seen" by the surface inspection or analysis device.

Film antireflectance occurs when an incident beam is partially reflected both from the top surface of the film and also from the bottom surface of the film, such that the two reflections are 180 degrees out of phase and of comparable amplitude and therefore cancel each other out. Two conditions are required for a single film to be antireflective. First, the film thickness must be equal to an odd multiple of the quarter-wavelength of the incident light, where this wavelength is measured in the medium of the film. Second, the index of refraction of the film must be equal to the square root of the product of the indices of refraction of the media on either side of the film. Multiple-layer antireflectives are also possible and are well known in the optical art.

"Antireflectance films" for the purposes of this specification will mean any film satisfying the requirements for antireflectance of a particular wavelength of incident light, including having required thicknesses and indices of refraction as well as being interposed between materials having the proper indices of refraction. For example, where a He—Ne laser operating at a wavelength of 0.6328 micrometers is employed as the scanning beam, a silicon nitride film having a thickness equal to an odd multiple of 0.6328/4 micrometers, is an antireflectance film when coating a substrate of silicon in air. The index of refraction of silicon is 3.87 and that of air is 1. The square root of the product of these two indices equals 1.97, which is approximately equal to the index of refraction of silicon nitride, 1.99, with all these indices of refraction measured at the wavelength of the scanned light, which in vacuum is 0.6328 micrometers.

Pursuant to the present invention, a calibration target for a surface analysis scanning device is provided which reduces the amount of light scattered by particle contamination on the target surface, which would otherwise interfere with the device calibration. The term "calibration target" as used in the remainder of this specification will reference target which is scanned by the surface analysis instrument for purposes of: (1) determining an operating parameter of the surface analysis device including sensitivity, count accuracy, and uniformity; (2) setting gain with respect to threshold settings; or (3) determining system noise levels.

In one embodiment a calibration target has a light absorbing substrate (such as silicon) which is completely covered with ah antireflectance film. The antireflectance film prevents light from being scattered by particles on the surface of the film and also prevents the reflection of any of the incident light from the surface. Therefore, the surface analysis device will detect no surface and no contaminating particles, even though the calibration target is actually present and may actually be contaminated with particles. Any signals produced by the device will represent only system noise, and therefore the noise level of the analysis device can be determined without interference from particles contaminating the calibration target. The antireflectance film may be removed from an area around the periphery of the target so that the surface analysis scanner can locate the target (or its edge margin) by reflected light from the uncoated substrate.

In another embodiment of the present invention, the calibration target includes a substrate having an antireflectance film and a number of reference features either deposited on the antireflectance film or etched through the film into the substrate. The reference features each scatter the incident light in a consistent fashion to simulate surface particles. Since the incident beam encounters an antireflectance film in areas other than those containing reference features, the photodetectors of the surface analysis device pick up only the intended feature. Other particles, then contaminating the film surface, will not be detected by the device and will therefore will not interfere with calibration, except on the rare occasions when such contaminating particles overlap the reference features.

Another embodiment of the calibration target in accordance with the present invention includes a body of transparent material having reference features imbedded therein. The reference features may be latex spheres, voids, or defects in medium homogeneity. The upper surface of the transparent material is coated with an antireflectance film. A substrate of light-absorbing material such as silicon supports the transparent material and another antireflectance film is interposed between the substrate and the transparent material. In this embodiment only incident light encountering a reference feature in the transparent material is scattered to be detected by the device. Particles which unavoidably contaminate the target on the antireflectance films are made to appear invisible to the device.

The present invention also includes a support structure for supporting a surface to be analyzed by a surface analysis scanner. This support structure prevents scanned light from being scattered by particles contaminating the support surface. In one embodiment, the support structure includes a substrate of light-absorbing material such as silicon, coated with an antireflectance film. The object to be analyzed rests on the antireflectance-coated substrate. Any light from the scanner which strikes the support is therefore not reflected and is not scattered by particles contaminating the support. In this embodiment the surface to be inspected may be irregularly shaped, such as irregularly shaped wafer fragments. The scanning beam scans past the edge of the surface without having any of the light reflected or scattered from the support and interfering with the functioning of the instrument.

In another embodiment the support comprises a silicon wafer which supports smaller objects to be inspected. The silicon wafer is coated with a silicon nitride antireflectance film with a portion of the nitride removed from an area around the periphery of the wafer. Reflectance of scanned light can be detected to determine the location of the wafer by the location of the exposed silicon surface.

The present invention also includes a structure for excluding regions of a surface from inspection by the surface analysis device without producing light signals which interfere with the analysis of the surface. In this embodiment an aperture is positioned between the source of the scanning beam and the surface to be inspected. Only light passing through the aperture encounters the surface to be inspected. The remaining portion of the scan is blocked by the material forming the aperture. To prevent light from reflecting from the aperture structure, the structure is made of a light-absorbing substrate coated with an antireflectance film. The scanned light does not reflect from the aperture structure, and also particles contaminating the structure surface do not scatter appreciable light. Therefore, the light striking the aperture structure is not picked up by the photodetectors and does not interfere with the functioning of the instrument.

The present invention also includes a light trap or baffle structure particularly for use with surface analysis devices. In one embodiment the light trap structure includes a substrate of light absorbing material coated with an antireflectance film. The antireflectance film prevents reflection of any of the particular incident light and also prevents particles contaminating the structure surface from scattering the incident light.

One object of the present invention is to provide a calibration target for a surface inspection scanner which reduces the amount of light scattered by particles contaminating the surface of the calibration target.

Another object of the invention is to provide a support structure for supporting objects being inspected by a surface analysis scanner, which reduces the amount of light scattered or reflected from the support surface which might interfere with the inspection of the intended surface.

A further object is to provide a large area support for supporting irregularly shaped objects for inspection by surface analysis scanners.

Another object is to provide a structure for excluding a portion of a surface from inspection by a surface analysis scanner.

Another object is to provide a structure for a light trap for use with surface analysis scanners, which reduces the amount of light scattered by particles contaminating the surface of the light trap and eliminating light from being reflected from the light trap.

These and other objects, advantages and features of the invention be apparent from the following description of preferred embodiments, considered along with the accompanying drawings.

DESCRIPTION OF THE PREFERRED EMBODIMENT

Figure 1:
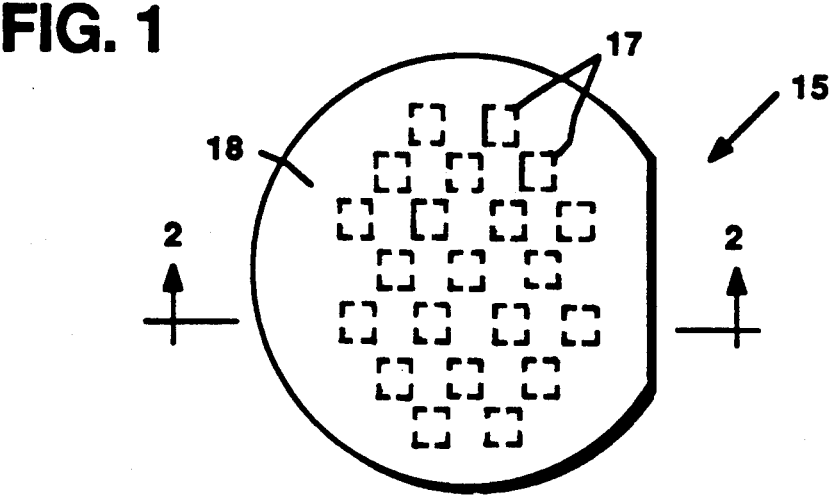
FIG. 1 is a plan view of a calibration target embodying the principles of the present invention.
Figure 2:
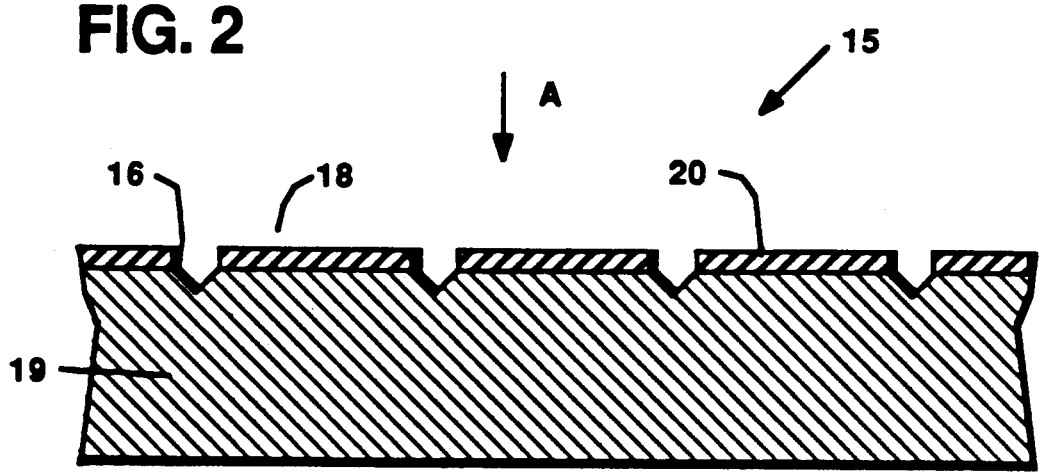
FIG. 2 is an enlarged view in section of a portion of the calibration target shown in FIG. 1, taken along the line 2—2 in FIG. 1, showing etched reference features.

FIG. 1 shows a calibration target generally indicated at 15 embodying the principles of the invention as used for a surface analysis scanner. The target 15 has numerous reference features 16 (See FIG. 2) in patterns 17 across its surface. The areas 18 between the reference points 16 are coated with an antireflectance film. FIG. 2 shows an enlarged cross section of the calibration target 15 in FIG. 1. In this embodiment the reference features 16 are etched into the target substrate 19. The antireflectance film 20 coats the entire surface of the substrate 19 other than area containing the reference features 16.

When a beam of light of the proper wavelength is directed onto the target 15 in the direction of arrow A in FIG. 2, and scanned across the surface of the target 15, light engaging the reference points 16 is scattered to simulate the light scattering of a particle resting on a surface. Light which engages the antireflectance film 20 is not reflected and does not interfere with the instrument readings. Also, any particles smaller than approximately five micrometers which contaminate the surface of the target 15 coated with the antireflectance film 20 do not scatter the incident beam sufficient to be detected. If the target 15 had no antireflectance film 20, particles larger than approximately 0.3 micrometers contaminating the target surface would scatter enough light for detection along with the reference points 16 and interfere with the device readings. Thus, the illustrated calibration target 15 scatters light only from the known reference features 16 which enables accurate testing of the surface analysis device particle counting function.

In order for the film 20 to be anti-reflective to approximately normal incident light, two conditions must be fulfilled. First, the film thickness must be approximately equal to an odd multiple of a quarter wavelength of the incident light, where the wavelength is measured in the medium of the film 20. Second, the index of refraction of the film 20 must be approximately equal to the square root of the product of the indices of refraction of the media on either side of the film 20, where all indices of refraction are measured at a wavelength of the particular incident light. For other angles of incidence, reference to standard college text books on optics give the somewhat different conditions to be fulfilled. Antireflectance conditions can also be established for more complex combinations of multiple films with certain thicknesses and refractivities.

For example, where a He—N laser operating at a wavelength of 0.6328 micrometers is used to produce the scanning beam to scan across a target 15 held in air ($n_O=1.0$), the film 20 may be a silicon nitride ($n_N=1.99$) film of a thickness equal to $1/(4) (0.6328)$ micrometers, and the substrate may be silicon ($n_{Si}=3.87$). Thus, the quantity $[(1.0)(3.87)]^{\frac{1}{2}}$ equals 1.97 which is approximately the index of refraction of silicon nitride to this particular wavelength of light.

Since the conditions for antireflectance are dependent on a particular wavelength of incident light, the light source utilized by the surface analysis device must be capable of producing substantially monochromatic light such as the He—Ne laser used in the previous example. Various other lasers and filtered He—Xe arc lamps, Sodium vapor lamps, and other light sources may also be used to provide the necessary monochromatic light.

Figure 3:
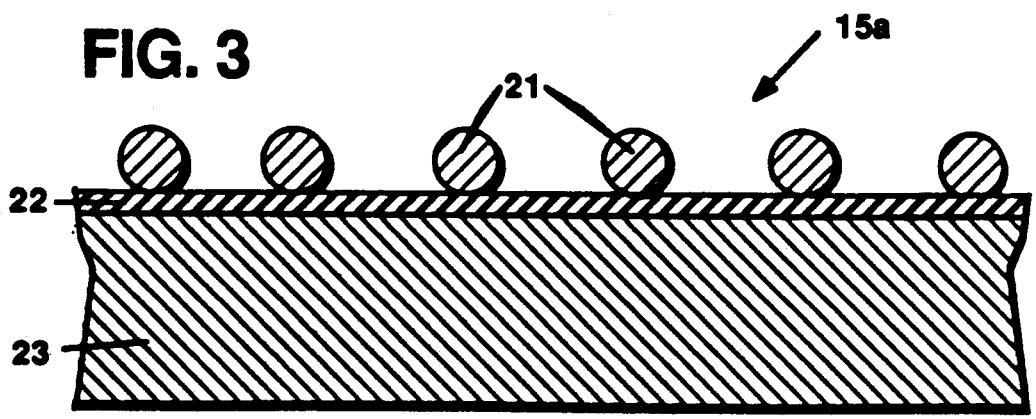
FIG. 3 is a view in section similar to FIG. 2 showing an alternative embodiment of the calibrating target with deposited reference features.

FIG. 3 shows an alternative embodiment of the calibration target 15a having reference features 21 deposited on an antireflectance film 22, which lies over a substrate 23. The deposited features 21 are very large particles compared to normally anticipated contaminating particles. For example, the deposited features 21 may be approximately spherical glass beads above twenty micrometers in diameter. Alternatively features may be deposited and etched metal film features of approximately cubical shape.

In the embodiment illustrate in FIG. 3, as well as the other targets having reference features, the size of the features does not correspond exactly to the equivalent particle on a bare substrate, but must be chosen to scatter the appropriate amount of light to match the desired threshold.

Figure 4:
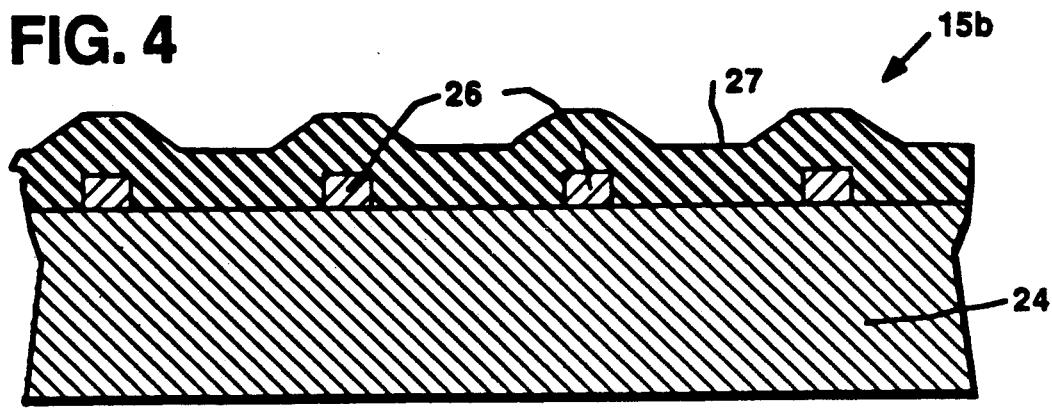
FIG. 4 is a view similar to FIG. 3 showing deposited and etched film features beneath an antireflectance film.

FIG. 4 shows another alternative calibration target 15b. The target 15b includes reference features 26 covered by an antireflectance film 27, the features 26 and film 27 having indices of refraction and thicknesses that cause maximum reflectance by the features 26. For example, where the surface analysis system using the target 15b utilizes a monochromatic scanning beam of 6328 Angstrom light, the substrate 24 may be a silicon wafer, the antireflectance film 27 may be silicon nitride approximately 795 Angstroms thick, and the features 26 may be etched from a silicon dioxide film approximately 1091 Angstroms thick. With these materials and thicknesses, the reflectivity to the scanning beam will be near maximum in areas where the antireflectance film 27 covers the features 26. However, the reflectivity will be near minimum in areas where the antireflectance film 27 covers only the substrate 24.

The Si/SiO$_2$/Si$_3$N$_4$ target structure of the previous example will function satisfactorily even if the thickness requirements are met only approximately as shown in Tables I and II. Table I lists the calculated percent reflectivity of the Si/SiO$_2$/Si$_3$N$_4$ structure versus thickness of the SiO$_2$ and Si$_3$N$_4$ with variations of plus or minus 50 and 100 Angstroms about the ideal one-quarter wave values. The reflectivity drops at most 2.4 percentage points, or 4.1% of nominal, over this range. Also, small changes in index or refraction would have a similarly small effect.

Table II lists the reflectivity of the nitride antireflectance film as a function of its thickness along with the contrast, defined as the ratio of the reflectance of the

TABLE I

| SiO$_2$ thickness (Angstroms) | Si$_3$N$_4$ thickness (Angstroms) | | | | |
|---|---|---|---|---|---|
| | 695 | 745 | 795 | 845 | 895 |
| | Reflectivity % | | | | |
| 991 | 55.29 | 56.42 | 57.18 | 57.29 | 57.05 |
| 1041 | 56.13 | 57.02 | 57.45 | 57.44 | 56.98 |
| 1091 | 56.69 | 57.35 | 57.58 | 57.34 | 56.66 |

TABLE I-continued

| SiO$_2$ thickness (Angstroms) | Si$_3$N$_4$ thickness (Angstroms) | | | | |
|---|---|---|---|---|---|
| | 695 | 745 | 795 | 845 | 895 |
| | Reflectivity % | | | | |
| 1141 | 57.00 | 57.34 | 57.43 | 56.98 | 56.07 |
| 1191 | 57.05 | 57.27 | 57.30 | 56.36 | 55.22 |

TABLE II

| Si$_3$N$_4$ thickness (Angstroms) | Reflectance % | Contrast |
|---|---|---|
| 695 | 1.93 | 28.9 |
| 745 | 0.48 | 120 |
| 795 | 0.014 | 4000 |
| 845 | 0.576 | 100 |
| 895 | 2.11 | 27.3 | nitride/oxide to that of the nitride alone. The contrast remains 100 to 1 or better for films within 50 Angstroms of the required one-quarter wave. Thus, thickness control of plus or minus five percent is adequate to provide increased contrast between the features 26 and the other areas and to provide relative freedom from noise due to accumulation of particles during use.

The Si/SiO$_2$/Si$_3$N$_4$ structure also has other desirable features. In fabrication, the selectivity of oxide etch to silicon is high so that the silicon oxide features can be formed without concern that over-etch will attack the substrate. Furthermore, the structure can be cleaned with harsh cleaning chemicals such as H$_2$SO$_4$:H$_2$O$_2$, 2:1, for example.

Figure 5:
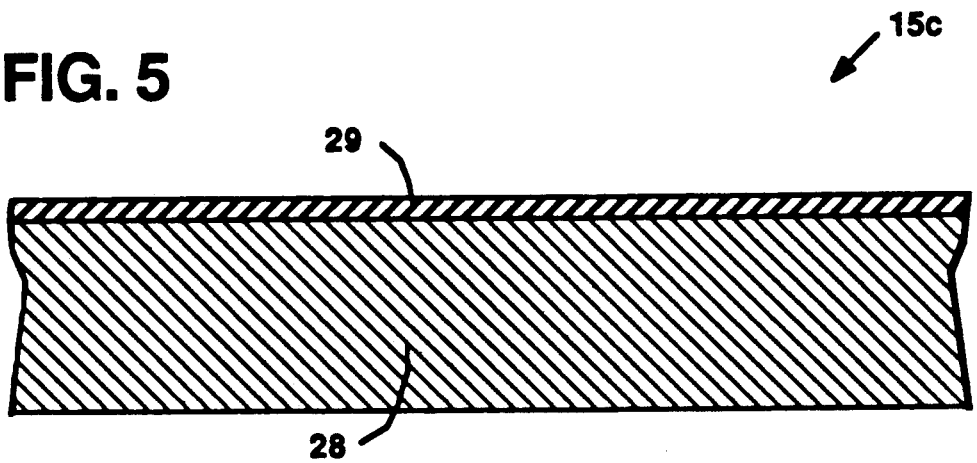
FIG. 5 is a similar view in section of another embodiment of the calibration target of the invention, used for determining noise level.

FIG. 5 illustrates a calibration target 15c according to the present invention of particular use in determining the noise level of a surface analysis scanner. The calibration target has a substrate 28, which is entirely coated with an antireflectance film 29. Since the film covers the entire substrate surface, incident light will not be reflected from the surface and will not be scattered sufficiently to be detected by the instrument. Therefore any apparent signals produced in the instrument will be from its own electrical noise, and this instrument noise level can easily be determined at a particular threshold setting.

Figure 6:
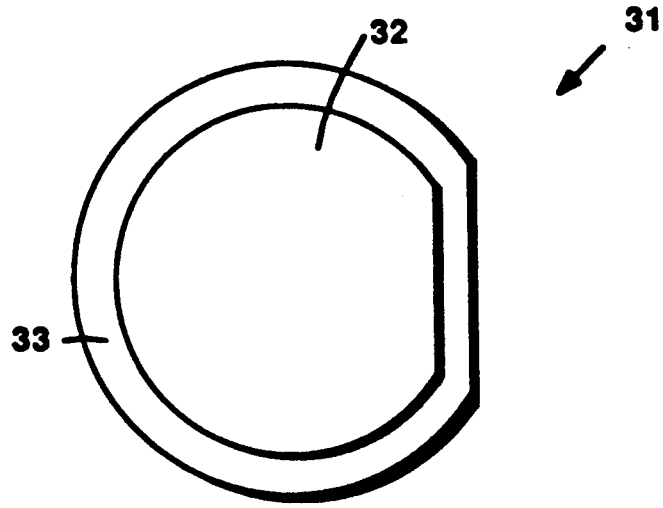
FIG. 6 is a plan view of another embodiment of a calibration target embodying the principles of the invention.

In the embodiment illustrated in FIG. 6, a calibration target 31 includes a substrate having an antireflectance-film-coated area 32 as previously discussed. However, in this embodiment the antireflectance film 32 has been removed around the edge of the target in a marginal area 33. This removal around the edge may be referred to as edge bead removal. Edge bead removal allows surface inspection devices which utilize reflectance data or edge scattering data to detect the outer perimeter of the area 33 where the antireflectance film 32 has been removed. Thus, edge bead removal allows the surface analysis device to locate the otherwise invisible calibration target 31. Also, note that there are other ways to avoid having the antireflective film at the edge of the substrate, such as using an edge mask during deposition or depositing additional films at its edge. For example, in the embodiment shown in FIG. 4, an SiO$_2$ film could be left in an area around the periphery of the target to be covered with the Si$_3$N$_4$ film to form a highly reflective edge bead.

Figure 7:
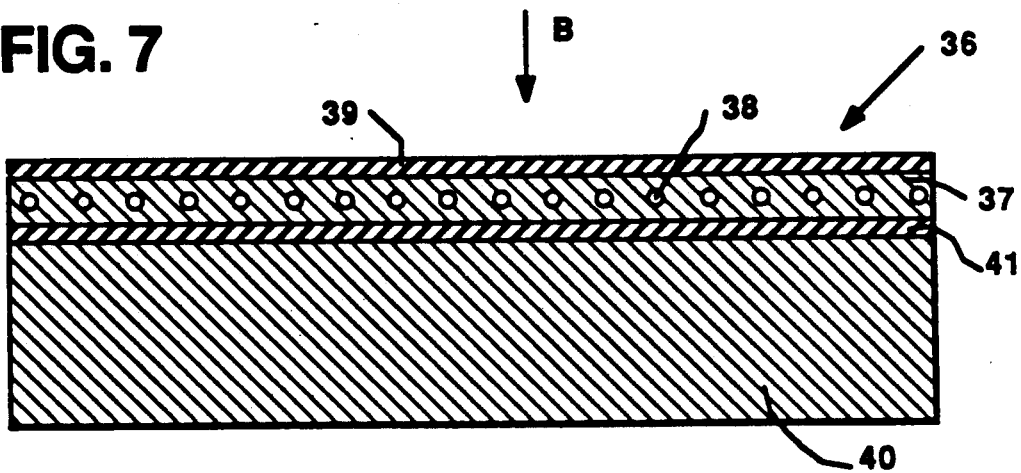
FIG. 7 is a view in section of another embodiment of the present calibration target.
Figure 7A:
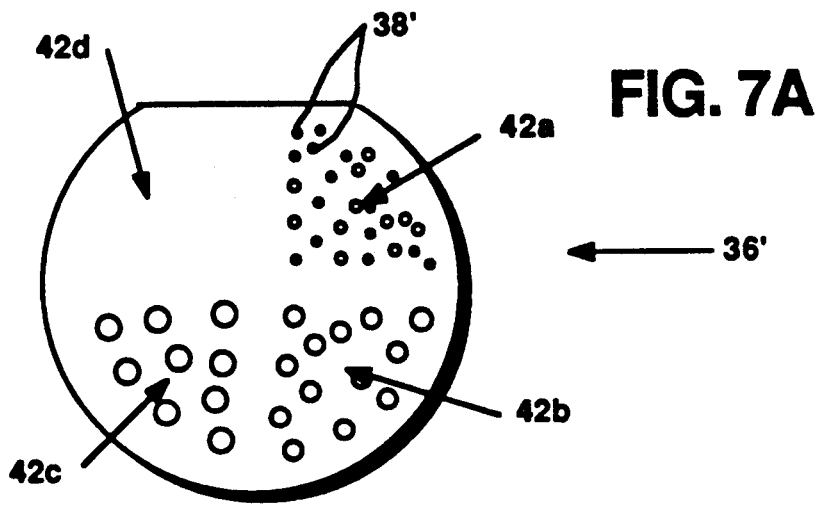
FIG. 7A is a top plan view of a calibration target similar to the target shown in FIG. 2, 3, or 7, showing an alternative distribution of features.

FIG. 7 illustrates another embodiment of a calibration target 36 of the present invention. This embodiment includes a block of transparent material 37, having imbedded reference features 38 dispersed therein. The upper surface of the transparent material is coated with an antireflectance film 39. The transparent material rests on a substrate of a light absorbing material 40 which is also coated with an antireflectance film 41. The reference features 38 in this embodiment may be latex spheres, voids, or defects in medium homogeneity. The reference features 38 may be randomly distributed throughout the transparent material and of substantially the same size, or as illustrated in FIG. 7A, the target 36' may be divided into quadrant 42a, 42b, and 42c, each having a different size of features 38', and quadrant 42d being void of such features. The arrangement of different sized features shown in FIG. 7a can be used not only in the target embodiment shown in FIG. 7, but also with the targets illustrated in FIGS. 2, 3 and 4.

Light incident on the target 36 in the direction of an arrow B in FIG. 7 will either engage a feature 38 or pass through the transparent material 37 without engaging a feature 38. The imbedded features 38 are sized large enough so that a portion of the light engaging a feature will be scattered and detected by the inspection device photo-detector (not shown). The two antireflectance films 39 and 41 are designed along with the thickness of the transparent material 37 so that light that does not engage a feature 38 passes through the first film 39 without reflection, the transparent material 37, the second film 41 without reflection, and into the absorbing medium substrate 40. As discussed previously, particles which may contaminate the first film surface, do not scatter the incident light due to the antireflectance film 39 and therefore do not interfere with the calibration of the surface analysis device. Although the illustrated target includes the second antireflectance film 41, this film may be omitted if substrate defects are rare.

Figure 8:
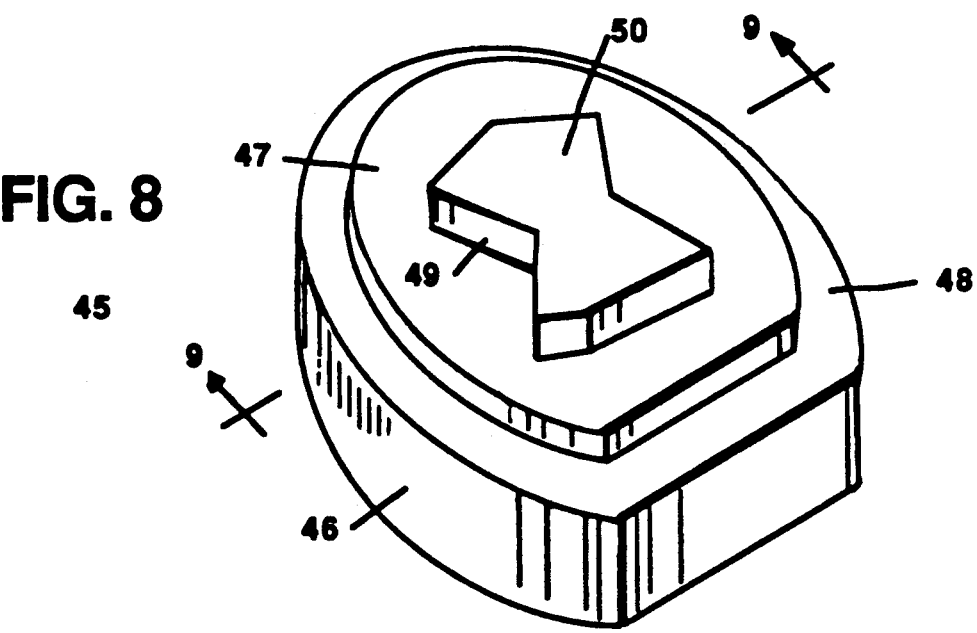
FIG. 8 is a view in perspective of a support member embodying the principles of the invention for supporting irregularly shaped objects to be inspected.
Figure 9:
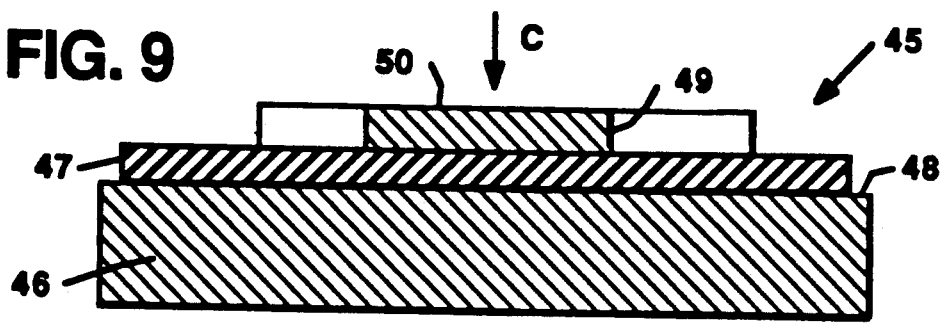
FIG. 9 is a view in section taken along line 9—9 in FIG. 8.

The present invention also includes a support structure for supporting irregularly shaped objects for surface inspection, an embodiment of which is illustrated in FIGS. 8 and 9. A support structure 45 includes a light-absorbing substrate 46 and an antireflectance film 47 which has been removed from an area 48 around the periphery of the support 45. An irregularly shaped object 49 with a surface 50 to be scanned is illustrated, being supported by the support structure 45 so that the surface 50 is held in the proper focal plane of the scanned light.

Light incident on the object 49 in the direction of an arrow C in FIG. 9, obtains surface information from the surface 50. However, light which is scanned across the support structure 45 will not be reflected to interfere with the readings from the surface 50. Furthermore, particles contaminating the surface of the support structure 45 will not scatter light, due to the presence of the antireflectance film 47.

As a result, the surface analysis instrument obtains information concerning the surface 50 without interference from light reflected or scattered from the support surface or contaminating particles thereon. This is particularly important in the case or irregularly shaped objects, because the scanning path is constant and overshoots the surface of interest to ensure complete information. The area 48 in which the antireflectance film 47 has been removed can be detected by the inspection instrument and allows the instrument to identify the otherwise invisible support structure 45 (that is, invisible to the particular scanned light).

Figure 10:
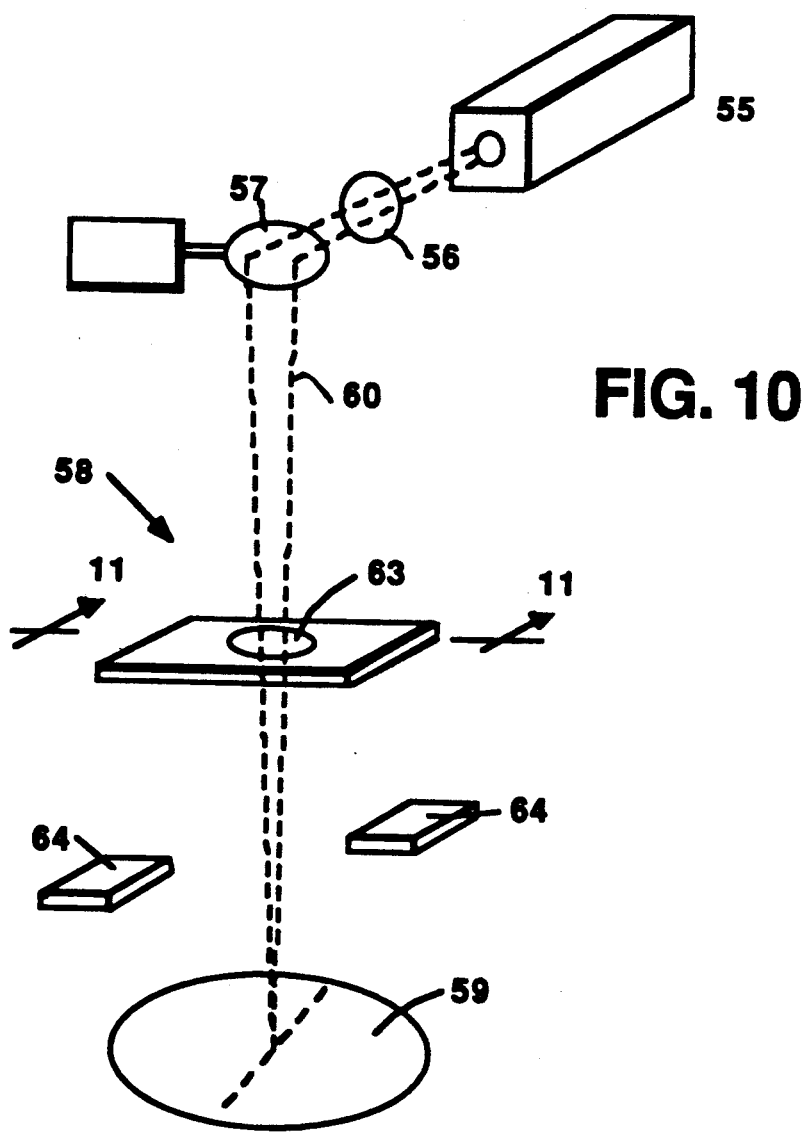
FIG. 10 is a generally schematic diagram of a surface inspection scanner with an aperture, also embodying the principles of the invention.
Figure 11:
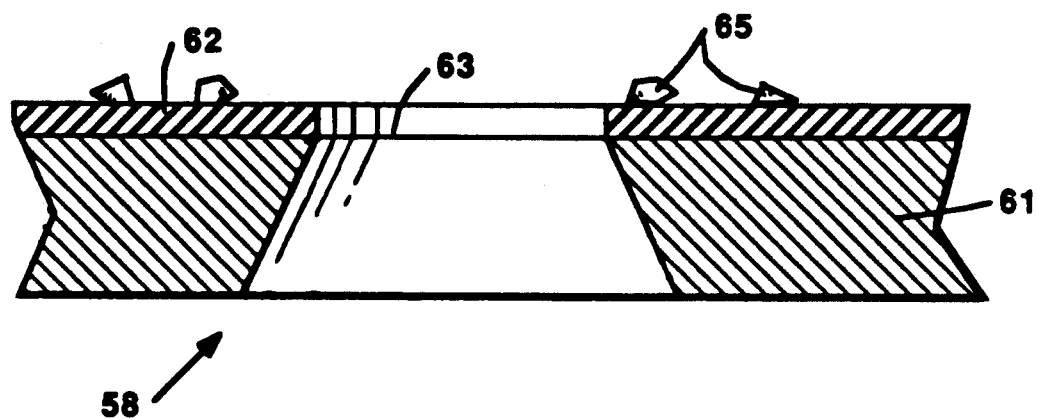
FIG. 11 is a an enlarged view in section taken along the line 11—11 in FIG. 10.

The invention also encompasses a structure for mechanically excluding a portion of a surface from inspection by a surface analysis instrument. Referring now to FIGS. 10 and 11, a beam 60 of light is produced by a beam source 55, and directed through focusing optics 56 to a scanning mirror 57, which scans the beam across an aperture structure 58 and a surface 59 to be inspected. As best seen in FIG. 11, an aperture structure 58 includes a substrate 61 of light absorbing material coated with an entireflectance film 62 and having an aperture 63.

Light which strikes the aperture structure 58 is not reflected from the structure surface or scattered by contaminating surface particles 65 due to the antireflectance film 62. The remainder of the scanned light passes through the aperture 63 and impinges on the surface 59 being analyzed. Detectors 64 detect scattered and reflected light to obtain information about the surface 59.

Figure 12:
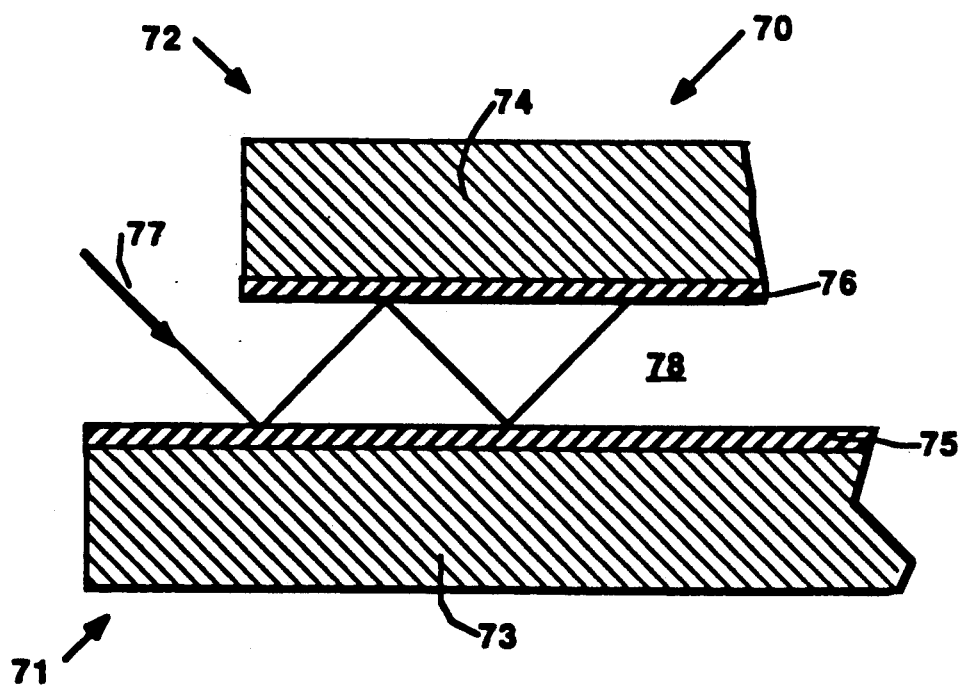
FIG. 12 is a view in section showing a light trap structure embodying the principles of the invention.

The invention also encompasses a light trap structure illustrated in FIG. 12 for use with surface analysis instruments as well as other optical devices. For example, to permit a particle counter to self-calibrate its own electrical noise level, a built-in light trap may be used to prevent light from being reflected internally to the counter causing additional noise. A calibrated target may be used as described above (see FIG. 5) or alternatively a light trap as shown in FIG. 12 may be used.

The light trap 70 includes two parallel antireflectance coated member 71 and 72, separated by space 78. The members 71 and 72 each comprise a light absorbing substrate 73 and 74 having an antireflectance film, 75 and 76 respectively, located on their opposing surfaces. As shown, an incident beam of light 77 strikes the member 71 and is substantially absorbed by substrate 73. Any energy reflected by the member 71 is absorbed upon further reflections. Particles contaminating the outer surface of the antireflective films 75 and 76 do not scatter light away from the trap 70 and thus do not interfere with calibration.

The above described preferred embodiment are intended to illustrate the principles of the invention, but not to limit the scope of the invention. Various other embodiments and modifications to these preferred embodiments may be made by those skilled in the art, without departing from the scope of the following claims.

What is claimed is:

1. A calibration target which reduces the amount of light scattered by particles contaminating the target's surface, for use with a surface analysis scanner of the type which detects particles adjacent to a surface by scanning a beam of monochromatic light across the surface and detecting light which is scattered by such adjacent particles, said target comprising:

a calibration target substrate having an upper surface;

an antireflectance film coating at least a portion of the upper surface of the calibration target substrate; and a plurality of reference features interposed between the upper surface of the calibration target substrate and the antireflectance film, wherein light from a surface analysis scanner which impinges upon the upper surface of the target is not substantially scattered by particles contaminating the target surface so that such contaminating particles are not detected by the surface analysis scanner and wherein the antireflectance film and the reference features are of such indices of refraction and thicknesses so as to produce maximum reflectance of the scanning beam from said features.

2. The calibration target as recited in claim 1, wherein the reference features are deposited and etched features.

3. The calibration target as recited in claim 2, wherein the reference features are made of silicon dioxide.

4. The calibration target as recited in claim 3, wherein the calibration target substrate is a silicon wafer.

5. The calibration target as recited in claim 4, wherein the antireflectance film is made of silicon nitride.

6. The calibration target as recited in claim 5, including a layer of silicon dioxide interposed between the silicon nitride film and the silicon wafer substrate around 7. A calibration target which reduces the amount of light scattered by particles contaminating the target's surface, for use with a surface analysis scanner of this type which detects particles adjacent to a surface by scanning a beam of monochromatic light across the surface and detecting light which is scattered by such adjacent particles, said target comprising:
 a calibration target substrate having an upper surface;
 an antireflectance film coating at least a portion of the upper surface of the calibration target substrate;
 a body of transparent material supported on the film;
 a plurality of reference features embedded in said transparent material for scattering scanned light from the upper surface of the target; and
 a second antireflectance film covering the upper surface of the transparent material,
 wherein light from a surface analysis scanner which impinges upon the upper surface of the target is not substantially scattered by particles contaminating the target surface so that such contaminating particles are not detected by the surface analysis scanner.

8. The calibration target as recited in claim 7, wherein each reference feature is a latex sphere.

9. The calibration target as recited in claim 7, wherein each reference feature is void in the transparent material.

10. The calibration target as recited in claim 7, wherein each reference feature is a defect in the transparent material homogeneity.

11. A calibration target which reduces the amount of light scattered by particles contaminating the target's surface, for use with a surface analysis scanner of the type which detects particles adjacent to a surface by scanning a beam of monochromatic light across the surface and detecting light which is scattered by such adjacent particles, said target comprising:
 a calibration target substrate having an upper surface; and
 an antireflectance film coating at least a portion of the upper surface of the calibration target substrate with no intervening layer therebetween, the antireflectance film being absent from an area around the periphery of the calibration target, so that a surface analysis scanner may detect the portion of the calibration target surface which is not antireflectance coated and thereby determine the position of the calibration target,
 wherein light from a surface analysis scanner which impinges upon the upper surface of the target is not substantially scattered by particles contaminating the target surface so that such contaminating particles are not detected by the surface analysis scanner.

* * * * *

UNITED STATES PATENT AND TRADEMARK OFFICE
CERTIFICATE OF CORRECTION

PATENT NO. : 5,004,340
DATED      : April 2, 1991
INVENTOR(S): Barclay J. Tullis and James B. Kruger It is certified that error appears in the above-identified patent and that said Letters Patent is hereby corrected as shown below:

Column 1, line 26 "Estak" should be --Estek--.

Column 3, line 58 "with ah antireflectance" should be --with an antireflectance--.

Column 4, lines 17-18 "will therefore will" should be --therefore will--.

Column 5, line 42 "invention be" should be --invention will be--.

Column 6, line 64 "He-N" should be --He-Ne--.

Column 10, line 7 "entireflectance" should be --antireflectance--; line 37 "embodiment" should be --embodiments--.

Column 11, Line 13 "around" should be --around the periphery of the upper surface of the silicon wafer, said layer of silicon dioxide having a thickness that produces near maximum reflectance of the scanning beam from the layer so that the periphery of the target may be detected by the surface analysis scanner.--

Signed and Sealed this

Sixteenth Day of March, 1993

Attest:

STEPHEN G. KUNIN

Attesting Officer

Acting Commissioner of Patents and Trademarks